United States Patent

Platzek et al.

[11] Patent Number: 6,136,841
[45] Date of Patent: Oct. 24, 2000

[54] 3-, 8-SUBSTITUTED DEUTEROPORPHYRIN DERIVATIVES, PHARMACEUTICAL AGENTS THAT CONTAIN THE LATTER, PROCESS FOR THEIR PRODUCTION AND THEIR USE IN PHOTODYNAMIC THERAPY AND MRI DIAGNOSIS

[75] Inventors: Johannes Platzek; Ulrich Niedballa; Bernd Raduechel, all of Berlin; Wolfgang Ebert, Mahlow; Hanns-Joachim Weinmann; Thomas Frenzel, both of Berlin, all of Germany

[73] Assignee: Schering Aktiengesellschaft, Berlin, Germany

[21] Appl. No.: 09/323,996

[22] Filed: Jun. 2, 1999

Related U.S. Application Data

[60] Provisional application No. 60/110,697, Dec. 3, 1998.

[30] Foreign Application Priority Data

Jun. 2, 1998 [DE] Germany .............. 198 25 512

[51] Int. Cl.$^7$ .................. A61K 49/00; C07D 487/22
[52] U.S. Cl. .................. 514/410; 540/145; 424/9.3; 424/9.362; 534/14; 534/15; 534/16; 534/10; 534/9; 534/8
[58] Field of Search .................. 540/145, 474; 514/410; 424/9.362, 9.3; 534/10–16

[56] References Cited

U.S. PATENT DOCUMENTS

| | | | |
|---|---|---|---|
| 5,053,503 | 10/1991 | Dean et al. | 540/474 |
| 5,275,801 | 1/1994 | Niedballa et al. | 424/540 |
| 5,849,259 | 12/1998 | Hilger et al. | 424/534 |

FOREIGN PATENT DOCUMENTS

| | | |
|---|---|---|
| 0 355 041 | 8/1989 | European Pat. Off. . |
| WO94/07894 | 4/1994 | WIPO . |

OTHER PUBLICATIONS

Nakajima et al., Japan, Nucl Med Biol 20(2), 231—7, 1993.

*Primary Examiner*—Mukund J. Shah
*Assistant Examiner*—Pavanaram K Sripada
*Attorney, Agent, or Firm*—Millen, White, Zelano & Branigan, PC

[57] ABSTRACT

3-,8-substituted deuteroporphyrin derivatives with various substituents in the 13- and 17-positions of the porphyrin skeleton are suitable as pharmaceutical agents for use in photodynamic therapy (PDT) and for MRI therapy monitoring.

20 Claims, No Drawings

3-, 8-SUBSTITUTED DEUTEROPORPHYRIN DERIVATIVES, PHARMACEUTICAL AGENTS THAT CONTAIN THE LATTER, PROCESS FOR THEIR PRODUCTION AND THEIR USE IN PHOTODYNAMIC THERAPY AND MRI DIAGNOSIS

The instant application claims benefit of U.S. Provisional Application No. 60/110,697, filed Dec. 3, 1998.

The invention relates to the subjects that are characterized in the claims, i.e., 3-, 8-substituted deuteroporphyrin derivatives, their use in photodynamic therapy and MRI diagnosis, pharmaceutical agents that contain these compounds, as well as a process for the production of these compounds and agents.

A promising process for the treatment of diseases, especially of tumors in tissues that are close to the surface or in hollow organs (bladder, esophagus), is photodynamic therapy (PDT). In this technique, a photosensitizing dye is used that accumulates in the tumor. Said dye is then irradiated, so that oxygen is converted into the highly reactive form of singlet-oxygen[1] $O_2$ under the action of the dye. This oxygen form is cytotoxic and kills the tissue (preferably tumor tissue) in its surrounding area.

Porphyrins also belong to the families of substances that are suitable for PDT: they accumulate in tumors and absorb light in a range in which living tissue is still fairly permeable, namely between 700–900 nm. Moreover, porphyrins exhibit yet other properties that are valuable for PDT: high yields in the excited triplet state, a long life of this state, and a good energy transfer to the oxygen with the formation of $^1O_2$.

Of the porphyrins (WO 92/06097, WO 97/20846; EP 0 811626; U.S. Pat. Nos. 5,633,275, 5,654,423, 5,675,001, 5,703,230, 5,705,622) and their derivatives, photofrin II (U.S. Pat. No. 4,882,234) is already on the market; others are in turn undergoing clinical trials. Photofrin II is a mixture of oligomers of hematoporphyrin, whereby ester and ether bonds connect the subunits to one another.

BPDMA (verteporphin, WO 97/48393), a benzoporphyrin derivative, is in clinical phase II. This compound is used to combat cancer of the skin and psoriasis and is especially successful in the case of age-related mascular degeneration (AMD), a disease that can lead to blindness.

For the treatment of esophageal or bronchial carcinomas, mTHPC (WO 95/29915) is being studied. MACE, a monoaspartyl-chlorine (CA 2121716; JP 09071531), also belongs to the group of chlorines. The patent literature mentions a group of chlorines that are suitable for PDT (see WO 97/19081, WO 97/32885; EP 0569113; U.S. Pat. Nos. 5,587,394, 5,648,485, 5,693,632).

In addition to the above-mentioned compounds, porphyrin-like unsaturated systems such as porphyrin-isomeric porphycene (WO 92/12636, WO 93/00087, WO 96/31451, WO 96/31452; U.S. Pat. Nos. 5,610,175, 5,637,608) and phtalocyanines (U.S. Pat. No. 5,686,439), texaphyrins (WO 95/10307; U.S. Pat. Nos. 5,591,422, 5,594,136, 5,599,923 5,599,928, 5,622,946), and purpurins are now also being studied. The common structural feature of the three last-mentioned classes is that they are metal derivatives. The absorption band in the long-wave range is frequently shifted by the metalization.

Paramagnetic metal ions have a negative effect on the life of the triplet state. The shortening of the life of this stage can exceed a factor of $10^3$. The triplet state is responsible for the energy transfer to the oxygen, but if the life is too short, singlet oxygen can no longer be formed.

Diamagnetic metal ions, however, stabilize the triplet state and thus increase the quantum yield of $^1O_2$. Zinc, tin, cadmium, aluminum, lutetium, indium, and yttrium are thus found as central ions in photosensitizing π-systems.

Zn-phthalocyanine is being studied as an active ingredient to combat age-related macular degeneration (AMD). A sulfonated phthalocyanine is being tested as an aluminum derivative to determine its action (photosense, Russia).

Tin-ethiopurpurin (WO 96/32094) is being studied with regard to its action against Kaposi's sarcoma, however.

As a representative of the expanded porphyrins, Lu-texaphyrin must be mentioned. The compound has a very long-lived triplet state and yields singlet oxygen in quantum yields of over 70%. It is being tested to determine its usability as an agent in the treatment of restenosis and is already in clinical phase I.

With the expanded porphyrins, rubyrins (U.S. Pat. No. 5,622,945), sapphyrins (U.S. Pat. No. 5,457,195), and porphyrazins (U.S. Pat. No. 5,675,001) can also be mentioned, which are also suitable for PDT owing to their absorption at 620–690 nm.

A very extensive description of chemical synthesis and properties with respect to suitability for photodynamic therapy is found in Chem. Rev. 1997, 97, 2267–2340, A. Jasat and D. Dolphin, Expanded Porphyrins and their Heterologs.

As already mentioned, the toxic action of the photosensitizer manifests itself where active ingredient and light collide. This means that concentration or longer retention in the skin results in an undesirable photosensitization of the skin. The duration of sensitization ranges from several days (MACE, BPDMA~3 days) to several weeks (m-THPC~3 weeks) to a month (photofrin II~30 days). In this time, exposure to light must be carefully avoided.

A significant drawback of the above-mentioned compounds that were previously used for PDT is that they are suitable only for therapy; simultaneous MRI-diagnostic monitoring of the success of the therapy is not possible with them. For this purpose, it is necessary to administer another paramagnetic substance which, moreover, must have a biodistribution that is as close to that of the therapeutic agent as possible. This requirement often cannot be met.

There is therefore a need for MRI-diagnostic agents for therapy monitoring of PDT. Compounds that are suitable both for PDT and for MRI-diagnostic therapy monitoring would be ideal.

It has been found, surprisingly enough, that porphyrin complexes that consist of a ligand of general formula I

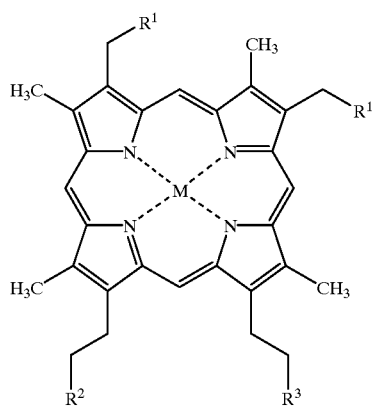

(I)

and at least one ion of an element of atomic numbers 20–32, 37–39, 42–51, or 57–83, in which M stands for two hydrogen atoms or a diamagnetic metal, $R^1$ stands for a hydrogen atom, for a straight-chain $C_1$–$C_6$ alkyl radical, a $C_7$–$C_{12}$ aralkyl radical or for a group OR', in which $R^1$ is a hydrogen atom or a $C_1$–$C_3$ alkyl radical, $R^2$ stands for $R^3$, a group —CO—Z or a group —(NH)$_o$—(A)$_q$—NH—D, in which Z is a group —OL, with L meaning an inorganic or organic cation or a $C_1$–$C_4$ alkyl radical, A means a phenylenoxy group or a $C_1$–$C_{12}$ alkylene or $C_7$–$C_{12}$ aralkylene group that is interrupted by one or more oxygen atoms, o and q, independently of one another, mean numbers 0 or 1, and D means a hydrogen atom or a group —CO—A—(COOL)$_o$—(H)$_m$, with m equal to 0 or 1 and provided that the sum of m and o is equal to 1, $R^3$ stands for a group —(C=Q)(NR$^4$)$_o$—(A)$_q$—(NR$^5$)—K, in which Q stands for an oxygen atom or for two hydrogen atoms, $R^4$ means a group —(A)$_q$—H and K means a complexing agent of general formula (IIa), (IIb), (IIc), (IId), or (IIe), whereby if K is a complexing agent of formula (IIa), $R^5$ has the same meaning as $R^4$, and if K is a complexing agent of formula (IIb), (IIc), (IId) or (IIe), $R^5$ has the same meaning as D, provided that a direct oxygen-nitrogen bond is not allowed, and K stands for a complexing agent of general formula (IIa), (IIb), (IIc), (IId) or (IIe),

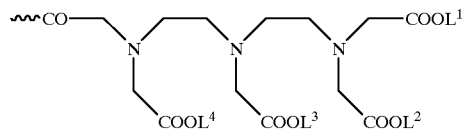

(IIa)

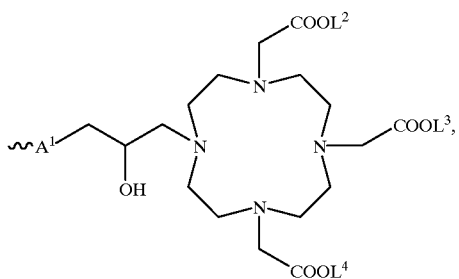

(IIb)

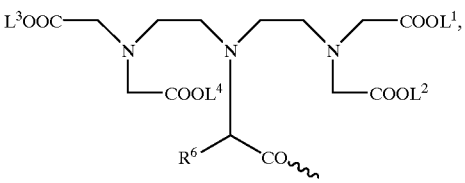

(IIc)

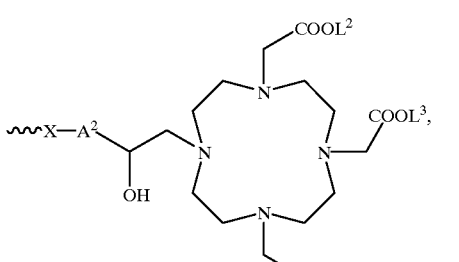

(IId)

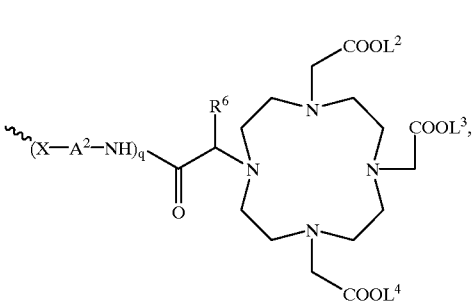

(IIe)

in which q has the above-indicated meaning, $A^1$ has the meaning that is indicated for A, $R^6$ stands for a hydrogen atom, a straight-chain or branched $C_1$–$C_7$ alkyl group, a phenyl or benzyl group, $A^2$ stands for a phenylene group, a —CH$_2$—NHCO—CH$_2$— CH(CH$_2$COOH)—C$_6$H$_4$ group, a phenylenoxy group, or a $C_1$–$C_{12}$ or $C_7$–$C_{12}$ alkylene group that is optionally interrupted by one or more oxygen atoms, 1 to 3 -NHCO groups, 1 to 3 -CONH groups and/or substituted with 1 to 3 —(CH$_2$)$_{0-5}$ COOH groups, X stands for a —CO group or an —NHCS group, and $L^1$, $L^2$, $L^3$ and $L^4$, independently of one another, stand for a hydrogen atom or a metal ion equivalent of an element of the above-mentioned atomic number, provided that at least two of these substituents stand for metal ion equivalents and that other anions are present to compensate for optionally present charges in the metalloporphyrin, and in which free carboxylic acid groups that are not required for complexing can also be present as salts with physiologically compatible inorganic and/or organic cations or as esters or as amides, are suitable, surprisingly enough, both for PDT and for MRI-diagnostic therapy monitoring.

The compounds of general formula I contain paramagnetic ions and are suitable for use in MRI diagnosis.

It is surprising, however, that despite the presence of these ions in the molecule, the quantum yield in the triplet state is so high that adequate singlet-oxygen is produced to operate successful PDT. According to the generally accepted wording of "long distance—electron/energy transfer" processes (Photoprocesses in Transition Metal Complexes, Biosystems and Other Molecules: Experiment and Theory, Publisher Elise Kochanski, Kluwer Academic Publishers, NATO DSI Series, p. 375; Photoinduced Electron Transfer, Vol. 1–4, Publisher M. A. Fox, M. Charon, Elsevir, New York 1988; M. D. Ward, Chem. Soc. Rev. 1997, 26, 365: T. Hayshi and H. Ogoshi, Chem. Soc. Rev. 1997, 26, 355; H. Dugas, Bioinorganic Chemistry, Springer Verlag, New York 1989; P. Tecilla et al., J. Am. Chem. Soc. 1990, 112, 9408; Y. Aoyama et al., J. Am. Chem. Soc. 1991, 113, 6233), a severe disruption of the triplet state—a drastic shortening of its life—would have been expected; and particularly the latter since it is known that interaction of photoactive centers in the molecules with donor or acceptor sites themselves takes place via hydrogen bridges, while even covalent bonds are present in the compounds of general formula I.

As other advantages of the compounds of general formula I, in contrast to the structurally similar compounds of EP 0355041, a) good compatibility b) very good water solubility c) high effectiveness in PDT d) good chemical stability in aqueous solution e) short half-life in the body f) complete excretion from the body g) high relaxivity can be cited.

For use of the agents according to the invention in NMR diagnosis, paramagnetic metal ions must be present in the complex. These are especially divalent and trivalent ions of the elements of atomic numbers 21–29, 42, 44 and 57–70. Suitable ions are, for example, chromium(III), manganese (II), manganese(III), iron(III), cobalt(II), cobalt(III), nickel (II), copper(II), praseodymium(II), neodymium(III), samarium(III) and ytterbium(III) ions. Because of their high magnetic moment, the gadolinium(III), dysprosium(III), manganese(II) and iron(III) ions are especially preferred. M preferably stands for two hydrogen atoms, $Zn^{2+}$, $Sn^{2+}$, $Sn^{4+}$, $Cd^{2+}$, $Mg^{2+}$, $Al^{3+}$, $Lu^{3+}$, $In^{3+}$, $B^{3+}$ and $Ga^{3+}$; especially preferably for two hydrogen atoms and $Zn^{2+}$.

The complexes according to the invention show, surprisingly enough, a considerably higher relaxivity compared to the structurally similar compounds that are known to date. Since the relaxivity can be regarded as a yardstick for the contrast medium action of a compound, a comparable, positive signal effect is possible even at a low dose with use of the complexes according to the invention in the area of NMR diagnosis. This significantly increases the safety margin, for which the product of relaxivity and compatibility can be considered as a guide value.

If an ion that is bonded in the porphyrin is present in a higher oxidation stage than +2, the excess charge(s) are compensated for by, e.g., anions of organic or inorganic acids, preferably by acetate, chloride, sulfate, nitrate, tartrate, succinate and maleate ions or by negative charge(s) that are present in $R^2$ and/or $R^3$.

The carboxyl groups that are not required for complexing of metal ions can optionally be present as esters, as amides or as salts of inorganic or organic bases. Suitable ester radicals are those with 1 to 6 C atoms, preferably ethyl esters; suitable inorganic cations are, for example, the lithium and the potassium ion, and especially the sodium ion. Suitable cations of organic bases are those of primary, secondary or tertiary amines, such as, for example, ethanolamine, diethanolamine, morpholine, glucamine, N,N-dimethylglucamine, especially meglumine.

In each case, $R^2$ and $R^3$ preferably stand for groups —CONHNHK, —CONH($CH_2$)$_2$NHK, —CONH($CH_2$)$_3$NHK, —CONH($CH_2$)$_4$NHK and —CONH(CH$)_2$O($CH_2$)$_2$NHK, whereby the first group is preferred, and $R^2$ and $R^3$ preferably stand for the same radical.

$A^2$ preferably stands for a —$CH_2$—, —$(CH_2)_2$—, —$CH_2OC_6H_4$-β, —$CH_2OCH_2$— —$C_6H_4$—, —$CH_2$—NHCO—$CH_2$—CH($CH_2$COOH)—$C_6H_4$-β, whereby β stands for the binding site to X.

X preferably stands for the CO group.

$R^6$ preferably stands for a hydrogen atom or a methyl group.

As a special compound, {mu-[{16,16'-[zinc(II)-7,12-diethyl-3,8,13,17-tetramethylporphyrin-2,18-diyl]bis[3,6,9-tris(carboxymethyl)-11,14-dioxo-3,6,9,12,13-pentaazahexadecanoato]}(8-)]}digadolinato(2-), disodium or the zinc-free compound can be mentioned.

As complexing agent radical K, preferably derivatives of diethylenetriaminepentaacetic acid and 1,4,7,10-tetraazacyclododecane-1,4,7-triacetic acid, which are bonded via a linker to the respective porphyrin, can be mentioned.

The production of the complex compounds of general formula I is carried out according to methods that are known in the literature (see, e.g., DE 4232925 for IIa and IIb; see, e.g., DE 19507822, DE 19580858 and DE 19507819 for IIIc; see, e.g., U.S. Pat. No. 5,053,503, WO 96/02669, WO 96/01655, EP 0430863, EP 255471, U.S. Pat. No. 5,277,895, EP 0232751, U.S. Pat. No. 4,885,363 for IId and IIe).

The compounds in which R2 and R3 stand for CONHNHK groups are preferred. The synthesis of the 3,3'-(7,12-diethyl-3,8,13,17-tetramethylporphyrin-2,18-diyl)di(propanohydrazide) that is required as an educt for this purpose is described in Z. Physiol Chem. 241, 209 (1936).

The introduction of the desired metals (e.g., Zn) into the porphyrins is carried out according to methods that are known in the literature (e.g., The Porphyrins, ed. D. Dolphin, Academic Press, New York 1980, Vol. V, p. 459; DE 4232925), whereby essentially the following can be mentioned:

a) The substitution of pyrrolic NH's (by heating the metal-free ligand with the corresponding metal salt, preferably acetate, optionally with the addition of acid-buffering agents, such as e.g., sodium acetate, in a polar solvent) or b) the "recomplexing," in which a metal that is already complexed by a ligand is displaced by the desired metal. As solvents, mainly polar solvents, such as, e.g., methanol, glacial acetic acid, dimethylformamide, chloroform and water are suitable.

The introduction of diamagnetic metal M into the porphyrin system can be carried out before or after linkage of complexing agent radical K. As a result, an especially flexible procedure for the synthesis of the compounds according to the invention is made possible.

The chelation of radical K is carried out in a way that is known in the literature (see, e.g., DE 34 01 052) by the metal oxide or metal salt (e.g., the nitrate, acetate, carbonate, chloride or sulfate) of the metal that is desired in each case being suspended or dissolved in polar solvents such as water or aqueous alcohols and being reacted with the corresponding amount of the complexing ligand. If desired, acidic hydrogen atoms or acid groups that are present can be substituted by cations of inorganic and/or organic bases or amino acids.

In this case, the neutralization is carried out with the aid of inorganic bases, such as, e.g., alkali or alkaline-earth hydroxides, -carbonates or -bicarbonates and/or organic bases such as, i.a., primary, secondary and tertiary amines, such as, e.g., ethanolamine, morpholine, glucamine, N-methyl- and N,N-dimethylglucamine, as well as basic amino acids, such as, e.g., lysine, arginine and ornithine or amides of originally neutral or acidic amino acids.

For the production of neutral complex compounds, enough of the desired bases can be added to, for example, the acidic complex salts in aqueous solution or suspension to ensure that the neutral point is reached. The solution that is obtained can then be evaporated to the dry state in a vacuum. It is commonly advantageous to precipitate the neutral salts that are formed by adding water-miscible solvents, such as, for example, lower alcohols (e.g., methanol, ethanol, isopropanol), lower ketones (e.g., acetone), polar ethers (e.g., tetrahydrofuran, dioxane, 1,2-dimethoxyethane) and thus to obtain easily isolated and readily purified crystallizates. It has proven especially advantageous to add the desired base as early as during the complexing of the reaction mixture and thus to eliminate a process step.

If the acidic complex compounds contain several free acid groups, it is often suitable to produce neutral mixed salts that contain both inorganic and organic cations as counterions.

This can happen, for example, by the complexing ligands being reacted in aqueous suspension or solution with the oxide or salt of the element that yields the central ion and half of the amount of an organic base that is required for neutralization, the complex salt that is formed being isolated, optionally purified and then mixed for complete neutralization with the required amount of inorganic base. The sequence in which the base is added can also be reversed.

Another way of obtaining neutral complex compounds consists in converting the remaining acid groups in the complex completely or partially into esters. This can happen by subsequent reaction on the finished complex (e.g., by exhaustive reaction of free carboxy groups with dimethylsulfate).

The production of the pharmaceutical agents according to the invention is also carried out in a way that is known in the art by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, e.g., tromethamine), small additions of complexing agents (such as, e.g., diethylenetriaminepentaacetic acid) or, if necessary, electrolytes such as, e.g., sodium chloride or, if necessary, antioxidants such as, e.g., ascorbic acid.

If suspensions or solutions of the agents according to the invention in water or in physiological salt solution are desired for enteral administration or other purposes, they are mixed with one or more adjuvant(s) that are commonly used in galenicals (e.g., methylcellulose, lactose, mannitol) and/or surfactant(s) (e.g., lecithins, Tween$^{(R)}$, Myrj$^{(R)}$) and/or flavoring substances for taste correction (e.g., ethereal oils).

In principle, it is also possible to produce the pharmaceutical agents according to the invention even without isolating the complex salts. In any case, special care must be taken to perform the chelation such that the salts and salt solutions according to the invention are virtually free of noncomplexed metal ions that have a toxic effect.

This can be ensured, for example, with the aid of color indicators such as xylenol orange by control titrations during the production process. The invention therefore also relates to the process for the production of complex compounds and their salts. As a final precaution, there remains purification of the isolated complex salt.

To avoid undesirable photoreactions of porphyrins, the compounds and agents according to the invention should be stored and handled as much as possible in a light-free environment.

The pharmaceutical agents according to the invention preferably contain 20 µmol/L to 200 mmol/L of the complex salt and are generally dosed in amounts of 0.01 µmol to 2 mmol/kg of body weight, both in their use for PDT and for therapy monitoring using MRI diagnosis. They are intended for enteral and parenteral administration or are administered with the methods of interventional radiology.

The agents according to the invention meet the varied requirements for suitability as agents for PDT and MRI contrast media. After administration, they are extremely well suited for enhancing the informational value of the image that is obtained with the aid of a nuclear spin tomograph by increasing the signal intensity. They also show the great effectiveness that is necessary to burden the body with the smallest possible amounts of foreign substances and the good compatibility that is necessary to maintain the noninvasive nature of the studies.

The good water-solubility of the agents according to the invention allows the production of highly concentrated solutions, so as to keep the volume burden of the circulation within justifiable limits and to compensate for the dilution by bodily fluid. In addition, the agents according to the invention show not only a high stability in vitro but also a surprisingly high stability in vivo, so that a release or an exchange of the ions, which are inherently toxic and not covalently bonded in the complexes, can be disregarded within the time that it takes for the contrast media to be completely excreted.

The invention is explained by the following examples.

EXAMPLE 1 a) [7,12-Diethyl-3,8,13,17-tetramethylporphyrin-2,18-dipropionylhydrazinato (2-)-K N21, K N22, K N23, K N24]-zinc 1190 mg (2 mmol) of 3,3'-(7,12-diethyl-3,8,13,17-tetramethylporphyrin-2,18-diyl)-di(propanohydrazide) (produced analogously to H. Fischer, E. Haarer and F. Stadler, Z. Physiol. Chem. 241, 209 (1936) and 427.18 mg (2 mmol) of zinc acetylacetonate-1 hydrate are heated in 150 ml of acetic acid/100 ml of chloroform for 5 hours to 80° C. Then, it is concentrated by evaporation in a vacuum, the residue is suspended in water, filtered off and washed with water. The dried crude product is recrystallized from pyridine/diethyl ether.

Yield: 1.25 g (95% of theory) of a reddish-brown powder

Elementary analysis (relative to anhydrous substance):

| Cld: | C 62.05 | H 6.13 | N 17.03 | Zn 9.94 |
| --- | --- | --- | --- | --- |
| Fnd: | C 63.27 | H 6.29 | N 16.88 | Zn 9.81 | b) [7,12-Diethyl-3,8,13,17-tetramethyl-2,18-bis {3,6,16-trioxo-8,11,14-tris(carboxymethyl) 17-oxa-4,5,8,11,14-pentaazanonadec-1-yl}porphyrinato (2-)]-zinc 806.8 mg (2 mmol) of 3-ethoxy-carbonylmethyl-6-[2-(2,6-dioxomorpholino)ethyl]-3,6-diazaoctanedioic acid (DTPA-monoethylester-monoanhydride) is suspended in 250 ml of absolute dimethylformamide. It is covered with a layer of nitrogen, 1.0 g (10 mmol) of triethylamine and 658 mg (1 mmol) of the title compound of Example 1a are added, and the resulting reaction mixture is stirred for 3 days at room temperature. After the reaction is completed, it is filtered, the solvent is drawn off in a vacuum, and the remaining oil is pulverized with 500 ml of diethyl ether. The precipitated solid is filtered off and washed with diethyl ether and n-hexane. For purification, it is chromatographed on silica gel RP-18 (eluant: $H_2O$/tetrahydrofuran: 0–30%).

Yield: 1.33 g (91% of theory) of a reddish-brown powder

Water content: 4.8%

Elementary analysis (relative to anhydrous substance):

| Cld: | C 54.11 | H 6.19 | N 13.39 | Zn 4.46 |
|------|---------|--------|---------|---------|
| Fnd: | C 54.31 | H 6.29 | N 13.29 | Zn 4.35 | c) [7,12-Diethyl-3,8,13,17-tetramethyl-2,18-bis{3,6,16-trioxo-8,11,14-tris(carboxymethyl)-4,5,8,11,14-pentaazahexadecanoato}porphinato(2-)]-zinc 1.3 g (0.887 mmol) of the ligand that is produced under Example 1b is dissolved in 400 ml of water. By adding 10 mol of aqueous sodium hydroxide solution, a pH of 13 is set, and it is stirred for 5 hours at room temperature. After the ester groups have been completely saponified, a pH of 3 is set with concentrated hydrochloric acid. It is evaporated to the dry state in a vacuum. The residue is chromatographed on RP 18 (eluant: $H_2O$/tetrahydrofuran/gradient).

Yield: 1.17 g (94% of theory) of a reddish-brown powder

Water content: 5.7%

Elementary analysis (relative to anhydrous substance):

| Cld: | C 52.86 | H 5.87 | N 13.92 | Zn 4.64 |
|------|---------|--------|---------|---------|
| Fnd: | C 52.68 | H 5.99 | N 13.81 | Zn 4.57 | d) {Mu-[(16,16'-[zinc(II)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), disodium 1.14 g (0.81 mmol) of the ligand that is produced under Example 1c is dissolved in 400 ml of water, and 427 mg (1.62 mmol) of gadolinium chloride and 2N aqueous sodium hydroxide solution are added alternately in portions, such that the pH of the reaction mixture constantly varies between 6.8 and 7.2. If all of the gadolinium chloride is added, stirring is continued overnight at room temperature. For working-up, the solvent is drawn off in a vacuum, and the residue is chromatographed on silica gel RP-18 (eluant: $H_2O$/tetrahydrofuran: 0–30%).

Yield: 1.412 g (99% of theory) of a reddish-brown powder

Water content: 7.4%

Elementary analysis (relative to anhydrous substance):

| Cld: | C 42.28 | H 4.24 | N 11.13 | Gd 17.86 | Na 2.61 | Zn 3.71 |
|------|---------|--------|---------|----------|---------|---------|
| Fnd: | C 42.35 | H 4.36 | N 11.01 | Gd 17.69 | Na 2.38 | Zn 3.58 |

EXAMPLE 2 a) [7,12-Diethyl-3,8,13,17-tetramethylporphyrin-2,18-dipropionylhydrazinato (2-)-K N21, K N22, K N23, K N24]-magnesium 1190 mg (2 mmol) of 3,3'-(7,12-diethyl-3,8,13,17-tetramethylporphyrin-2,18-diyl)-di(propanohydrazide) (produced analogously to H. Fischer, E. Haarer and F. Stadler, Z. Physiol. Chem. 241, 209; 1936) and 517.12 mg (2 mmol) of magnesium acetyl acetonate-dihydrate are heated in 150 ml of acetic acid/100 ml of chloroform for 5 hours to 80° C. Then, it is concentrated by evaporation in a vacuum, the residue is suspended in water, filtered off and washed with water. The dried crude product is recrystallized from pyridine/diethyl ether.

Yield: 1.16 g (94% of theory) of a reddish-brown powder

Elementary analysis (relative to anhydrous substance):

| Cld: | C 66.18 | H 6.53 | N 18.16 | Mg 3.94 |
|------|---------|--------|---------|---------|
| Fnd: | C 66.01 | H 6.49 | N 18.02 | Mg 3.87 | b) [7,12-Diethyl-3,8,13,17-tetramethyl-2,18-bis{3,6,16-trioxo-8,11,14-tris(carboxymethyl) 17-oxa-4,5,8,11,14-pentaazanonadec-1-yl}porphyrinato (2-)]-magnesium 806.8 mg (2 mmol) of 3-ethoxy-carbonylmethyl-6-[2-(2,6-dioxomorpholino)ethyl]-3,6-diazaoctanedioic acid (DTPA-monoethyl ester-monoanhydride) is suspended in 250 ml of absolute dimethylformamide. It is covered with a layer of nitrogen, 1.0 g (10 mmol) of triethylamine and 658 mg (1 mmol) of the title compound of Example 2a are added, and the resulting reaction mixture is stirred for 3 days at room temperature. After the reaction is completed, it is filtered, the solvent is drawn off in a vacuum, and the remaining oil is pulverized with 500 ml of diethyl ether. The precipitated solid is filtered off and washed with diethyl ether and n-hexane. For purification, it is chromatographed on silica gel RP-18 (eluant: $H_2O$/tetrahydrofuran: 0–30%).

Yield: 1.28 g (90% of theory) of a reddish-brown powder

Water content: 6.1%

Elementary analysis (relative to anhydrous substance):

| Cld: | C 55.68 | H 6.37 | N 13.77 | Mg 1.71 |
|------|---------|--------|---------|---------|
| Fnd: | C 55.55 | H 6.48 | N 13.68 | Mg 1.61 | c) [7,12-Diethyl-3,8,13,17-tetramethyl-2,18-bis{3,6,16-trioxo-8,11,14-tris(carboxymethyl)-4,5,8,11,14-pentaazahexadecanoato}porphinato(2-)]-magnesium 1.25 g (0.878 mmol) of the ligand that is produced under Example 2b is dissolved in 400 ml of water. By adding 10 mol of aqueous sodium hydroxide solution, a pH of 13 is set, and it is stirred for 5 hours at room temperature. After the ester groups have been completely saponified, a pH of 3 is set with concentrated hydrochloric acid. It is evaporated to the dry state in a vacuum. The residue is chromatographed on RP 18 (eluant: H$_2$O/tetrahydrofuran/gradient).

Yield: 1.12 g (93% of theory) of a reddish-brown powder

Water content: 5.8%

Elementary analysis (relative to anhydrous substance):

| Cld: | C 54.45 | H 6.04 | N 14.34 | Mg 1.78 |
|---|---|---|---|---|
| Fnd: | C 54.51 | H 6.21 | N 14.17 | Mg 1.63 | d) {Mu-[{16,16'-[magnesium(II)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), -disodium 1.09 g (0.797 mmol) of the ligand that is produced under Example 2c is dissolved in 400 ml of water, and 420.2 mg (1.594 mmol) of gadolinium chloride and 2N aqueous sodium hydroxide solution are added alternately in portions, such that the pH of the reaction mixture constantly varies between 6.8 and 7.2. If all of the gadolinium chloride is added, stirring is continued overnight at room temperature. For working-up, the solvent is drawn off in a vacuum, and the residue is chromatographed on silica gel RP-18 (eluant: H$_2$O/tetrahydrofuran: 0–30%).

Yield: 1.36 g (99% of theory) of a reddish-brown powder

Water content: 7.2%

Elementary analysis (relative to anhydrous substance):

| Cld: | C 43.20 | H 4.34 | N 11.40 | Gd 18.28 | Mg 1.41 | Na 2.67 |
|---|---|---|---|---|---|---|
| Fnd: | C 43.10 | H 4.51 | N 11.28 | Gd 18.13 | Mg 1.36 | Na 2.41 |

EXAMPLE 3 a) Acetato[7,12-diethyl-3,8,13,17-tetramethylporphyrin-2,18-dipropionylhydrazinato(2-)-K N21, K N22, K N23, K N24]-aluminum 1190 mg (2 mmol) of 3,3'-(7,12-diethyl-3,8,13,17-tetramethylporphyrin-2,18-diyl)-di(propanohydrazide) (produced analogously to H. Fischer, E. Haarer and F. Stadler, Z. Physiol. Chem. 241, 209 (1936) and 648.62 mg (2 mmol) of aluminum acetylacetonate are heated in 150 ml of acetic acid/100 ml of chloroform for 5 hours to 80° C. Then, it is concentrated by evaporation in a vacuum, the residue is suspended in water, filtered off and washed with water. The dried crude product is recrystallized from pyridine/diethyl ether.

Yield: 1.30 g (96% of theory) of a reddish-brown powder

Elementary analysis (relative to anhydrous substance):

| Cld: | C 63.70 | H 6.39 | N 16.51 | Al 3.98 |
|---|---|---|---|---|
| Fnd: | C 63.58 | H 6.51 | N 16.37 | Al 3.81 | b) Acetato[7,12-diethyl-3,8,13,17-tetramethyl-2,18-bis{3,6,18-trioxo-8,11,14 tris(carboxymethyl)-17-oxa-4,5,8,11,14-pentaazanonadec-1-yl}porphinato(3-)]-aluminum 806.8 mg (2 mmol) of 3-ethoxy-carbonylmethyl-6-[2-(2,6-dioxomorpholino)ethyl]-3,6-diaza octanedioic acid (DTPA-monoethyl ester-monoanhydride) is suspended in 250 ml of absolute dimethylformamide. It is covered with a layer of nitrogen, 1.0 g (10 mmol) of triethylamine and 678.77 mg (1 mmol) of the title compound of Example 3a are added, and the resulting reaction mixture is stirred for 3 days at room temperature. After the reaction is completed, it is filtered, the solvent is drawn off in a vacuum, and the remaining oil is pulverized with 500 ml of diethyl ether. The precipitated solid is filtered off and washed with diethyl ether and n-hexane. For purification, it is chromatographed on silica gel RP-18 (eluant: H$_2$O/tetrahydrofuran: 0–30%).

Yield: 1.29 g (87% of theory) of a reddish-brown powder

Water content: 6.9%

Elementary analysis (relative to anhydrous substance):

| Cld: | C 54.98 | H 6.31 | N 13.20 | Al 1.82 |
|---|---|---|---|---|
| Fnd: | C 54.88 | H 6.52 | N 13.10 | Al 1.67 | c) Chloro[7,12-diethyl-3,8,13,17-tetramethyl-2,18-bis{3,6,18-trioxo-8,11,14 tris(carboxymethyl)-4,5,8,11,14-pentaazahexadecanoato}porphinato(3-)]-aluminum 1.26 g (0.848 mmol) of the ligand that is produced under Example 3b is dissolved in 400 ml of water. By adding 10 mol of aqueous sodium hydroxide solution, a pH of 13 is set, and it is stirred for 5 hours at room temperature. After the ester groups have been completely saponified, a pH of 3 is set with concentrated hydrochloric acid. It is evaporated to the dry state in a vacuum. The residue is chromatographed on RP 18 (eluant: H$_2$O/tetrahydrofuran/gradient).

Yield: 1.09 g (91% of theory) of a reddish-brown powder

Water content: 5.3%

Elementary analysis (relative to anhydrous substance):

| Cld: | C 52.97 | H 5.88 | N 13.95 | Al 1.92 | Cl 2.52 |
|---|---|---|---|---|---|
| Fnd: | C 52.90 | H 6.03 | N 13.87 | Al 1.83 | Cl 2.43 | d) {Mu-[{16,16'-[chloroaluminium(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), disodium 1.05 g (0.747 mmol) of the ligand that is produced under Example 3c is dissolved in 400 ml of water, and 393.82 mg (1.494 mmol) of gadolinium chloride and 2N aqueous sodium hydroxide solution are added alternately in portions, such that the pH of the reaction mixture constantly varies between 6.8 and 7.2. If all of the gadolinium chloride is added, stirring is continued overnight at room temperature. For working-up, the solvent is drawn off in a vacuum, and the residue is chromatographed on silica gel RP-18 (eluant: H$_2$O/tetrahydrofuran: 0–30%).

Yield: 1.30 g (99% of theory) of a reddish-brown powder

Water content: 4.8%

Elementary analysis (relative to anhydrous substance):

| Cld: | C 42.35 | H 4.24 | N 11.15 | Gd 17.89 | Al 1.53 | Cl 2.02 | Na 2.62 |
|---|---|---|---|---|---|---|---|
| Fnd: | C 42.48 | H 4.38 | N 11.03 | Gd 17.77 | Al 1.47 | Cl 1.87 | Na 2.51 |

EXAMPLE 4 a) Acetato[7,12-diethyl-3,8,13,17-tetramethylporphyrin-2,18-dipropionylhydrazinato(2-)-K N21, K N22, K N23, K N24]-lutetium 1190 mg (2 mmol) of 3,3'-(7,12-diethyl-3,8,13,17-tetramethylporphyrin-2,18-diyl)-di(propanohydrazide) (produced analogously to H. Fischer, E. Haarer and F. Stadler, Z. Physiol. Chem. 241, 209 (1936) and 944.6 mg (2 mmol) of lutetium acetylacetonate are heated in 150 ml of acetic acid/100 ml of chloroform for 5 hours to 80° C. Then, it is concentrated by evaporation in a vacuum, the residue is suspended in water, filtered off and washed with water. The dried crude product is recrystallized from pyridine/diethyl ether.

Yield: 1.50 g (91% of theory) of a reddish-brown powder
Elementary analysis (relative to anhydrous substance):

| Cld: | C 52.30 | H 5.24 | N 13.55 | Lu 21.16 |
|---|---|---|---|---|
| Fnd: | C 52.15 | H 5.18 | N 13.47 | Lu 21.03 | b) Acetato[7,12-diethyl-3,8,13,17-tetramethyl-2,18-bis{3,6,18-trioxo-8,11,14-tris(carboxymethyl)-17-oxa-4,5,8,11,14-pentaazanonadec-1-yl}-porphinato (3-)]-lutetium 806.8 mg (2 mmol) of 3-ethoxy-carbonylmethyl-6-[2-(2,6-dioxomorpholino)ethyl]-3,6-diaza octanedioic acid (DTPA-monoethylester-monoanhydride) is suspended in 250 ml of absolute dimethylformamide. It is covered with a layer of nitrogen, 1.01 g (10 mmol) of triethylamine and 826.76 mg (1 mmol) of the title compound of Example 4a are added, and the resulting reaction mixture is stirred for 3 days at room temperature. After the reaction is completed, it is filtered, the solvent is drawn off in a vacuum, and the remaining oil is pulverized with 500 ml of diethyl ether. The precipitated solid is filtered off and washed with diethyl ether and n-hexane. For purification, it is chromatographed on silica gel RP-18 (eluant: H₂O/tetrahydrofuran: 0–30%).

Yield: 1.42 g (87% of theory) of a reddish-brown powder
Water content: 4.6%
Elementary analysis (relative to anhydrous substance):

| Cld: | C 50.00 | H 5.74 | N 12.00 | Lu 10.71 |
|---|---|---|---|---|
| Fnd: | C 49.81 | H 5.85 | N 11.87 | Lu 10.58 | c) Chloro [7,12-diethyl-3,8,13,17-tetramethyl-2,18-bis{3,6,18-trioxo-8,11,14-tris(carboxymethyl)-4,5,8,11,14-pentaazahexadecanoato}porphinato (3-)]-lutetium 1.39 g (0.851 mmol) of the ligand that is produced under Example 4b is dissolved in 400 ml of water. By adding 10 mol of aqueous sodium hydroxide solution, a pH of 13 is set, and it is stirred for 5 hours at room temperature. After the ester groups have been completely saponified, a pH of 3 is set with concentrated hydrochloric acid. It is evaporated to the dry state in a vacuum. The residue is chromatographed on RP 18 (eluant: H₂O/tetrahydrofuran/gradient).

Yield: 1.22 g (92% of theory) of a reddish-brown powder
Water content: 5.3%
Elementary analysis (relative to anhydrous substance):

| Cld: | C 47.93 | H 5.32 | N 12.62 | Cl 2.28 | Lu 11.26 |
|---|---|---|---|---|---|
| Fnd: | C 47.81 | H 5.47 | N 12.48 | Cl 2.14 | Lu 11.14 | d) {Mu-[{16,16'-[chlorolutetium(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), disodium 1.19 g (0.766 mmol) of the ligand that is produced under Example 4c is dissolved in 400 ml of water, and 403.8 mg (1.532 mmol) of gadolinium chloride and 2N aqueous sodium hydroxide solution are added alternately in portions such that the pH of the reaction mixture constantly varies between 6.8 and 7.2. If all of the gadolinium chloride is added, stirring is continued overnight at room temperature. For working-up, the solvent is drawn off in a vacuum, and the residue is chromatographed on silica gel RP-18 (eluant: H₂O/tetrahydrofuran: 0–30%).

Yield: 1.44 g (99% of theory) of a reddish-brown powder
Water content: 6.5%
Elementary analysis (relative to anhydrous substance):

| Cld: | C 39.07 | H 3.91 | N 10.29 | Gd 16.50 | Cl 1.86 | Lu 9.18 | Na 2.41 |
|---|---|---|---|---|---|---|---|
| Fnd: | C 38.98 | H 4.13 | N 10.14 | Gd 16.37 | Cl 1.78 | Lu 9.03 | Na 2.35 |

EXAMPLE 5 a) {7,12-Diethyl-3,8,13,17-tetramethyl-2,18-bis[15,15-dimethyl-3,6,13-trioxo-8-(2-{N,N-bis[(t butoxycarbonyl)methyl]amino}-ethyl)-11-[(t-butoxycarbonyl)-methyl]14-oxa-4,5,8,11-tetraazahexadec-1-yl}-porphyrin 8.31 g (13.45 mmol) of 3,9-bis(t-butoxycarbonylmethyl)-6-carboxymethyl-3,6,9-triaza-undecanedioic acid-di-t-butyl ester, produced according to DE 19507819, Example 1f, and 2.09 g (15 mmol) of 4-nitrophenol are dissolved in 60 ml of dimethylformamide, and 5.16 g (25 mmol) of N,N'-dicyclohexylcarbodiimide is added at 0° C. It is stirred for 3 hours at 0° C., then overnight at room temperature. 2 g (3.36 mmol) of 3,3'-(7,12-diethyl-3,8,13,17-tetramethylporphyrin-2,18-diyl)-di(propanohydrazide), produced according to H. Fischer, E. Haarer and F. Stadler, Z. Physiol. Chem., 241, 209 (1936), (dissolved in 50 ml of pyridine), is added in drops to the active ester solution that is thus produced, and it is stirred overnight. It is evaporated to the dry state in a vacuum, and the residue is chromatographed on silica gel (mobile solvent: dichloromethane/2-propanol=20:1).

Yield: 5.24 g (87% of theory) of a dark-brown solid

Elementary analysis (relative to anhydrous substance):

| Cld: | C 62.92 | H 8.31 | N 10.93 |
|---|---|---|---|
| Fnd: | C 62.81 | H 8.45 | N 10.80 | b) {Mu-[{13,13'-[7,12-diethyl-3,8,13,17-tetramethyl-porphyrin-2,18-diyl]-bis{3-carboxymethyl-6-(2-{N,N-bis[(carboxy)methyl]amino}ethyl)-8,11-dioxo-3,6,9,10-tetraazatridecanoato]}(8-)]}digadolinato(2-), disodium 5 g (2.79 mmol) of the title compound of Example 5a is dissolved in 100 ml of trifluoroacetic acid and stirred for 8 hours at room temperature. It is evaporated to the dry state in a vacuum. The ligand that is thus obtained is dissolved in 100 ml of water, and 1.01 g (2.79 mmol) of gadolinium oxide is added. It is stirred at 60° C., and the pH is kept at 5 by adding 1N aqueous sodium hydroxide solution. The solution is filtered, and the filtrate is set at pH 7.2 with 1N aqueous sodium hydroxide solution. Then, it is chromatographed on RP 18 (mobile solvent: gradient consisting of water/acetonitrile).

Yield: 4.49 g (95% of theory) of an amorphous solid

Water content: 10.3%

Elementary analysis (relative to anhydrous substance):

| Cld: | C 43.86 | H 4.51 | N 11.55 | Gd 18.52 | Na 2.71 |
|---|---|---|---|---|---|
| Fnd: | C 43.61 | H 4.70 | N 11.38 | Gd 18.37 | Na 2.50 |

EXAMPLE 6

{10,10'-(My-{10,10'-(7,12-diethyl-3,8,13,17-tetramethylporphyrin-2,18-diyl)bis[(1RS)-1-methyl-2,5,8-trioxo-3,6,7-triaza-dec-1-yl]})bis[1,4,7,10-tetraazacyclododecane-1,4,7-triacetato(3-)]}digadolinium 8.47 g (13.45 mmol) of the Gd complex of 10-(4-carboxy-2-oxo-3-aza-1-methyl-butyl)-1,4,7,10-tetraazacyclododecane-1,4,7-triacetic acid, 0.64 g of lithium chloride (15 mmol) and 2.09 g (15 mmol) of 4-nitrophenol are dissolved in 100 ml of dimethyl sulfoxide at 50° C. After cooling to room temperature, 5.16 g (25 mmol) of N,N'-dicyclohexylcarbodiimide is added and preactivated for 12 hours. 2 g (3.36 mmol) of 3,3'-(7,12-diethyl-3,8,13,17-tetramethylporphyrin-2,18-diyl)di(propanohydrazide) and 0.71 g (7 mmol) of triethylamine are added to the solution that is thus produced, and it is stirred overnight at room temperature. The suspension that is obtained is then mixed with sufficient acetone until precipitation occurs, the precipitate is suctioned off, dried, taken up in water, insoluble dicyclohexylurea is filtered out, and the filtrate is chromatographed on RP 18 (mobile solvent: gradient consisting of tetrahydrofuran/water).

Yield: 5.07 g (83% of theory) of a dark brown amorphous powder

Water content: 7.9%

Elementary analysis (relative to anhydrous substance):

| Cld: | C 47.56 | H 5.43 | N 13.87 | Gd 17.30 |
|---|---|---|---|---|
| Fnd: | C 47.42 | H 5.53 | N 13.68 | Gd 17.15 |

EXAMPLE 7 a) Conjugate consisting of 3,3'-(7,12-diethyl-3,8,13,17-tetramethylporphyrin-2,18-diyl)di(propanohydrazide) and 10-[7-(4-isothiocyanatophenyl)-2-hydroxy-5-oxo-7-(carboxymethyl)-4-aza-heptyl)]-1,4,7-tris(carboxylatomethyl)-1,4,7-tris(carboxylatomethyl)-1,4,7,10-tetraazacyclododecane, gadolinium complex, sodium salt ({10,10'-{My-[(7,12-diethyl-3,8,13,17-tetramethylporphyrin-2,18-diyl)bis{(1-oxopropane-3,1-diyl)hydrazino-thiocarbonylamino-4,1-phenylene[(3RS)-3-carboxymethyl-1-oxopropane-3,1-diyl]amino(2-hydroxypropane-3,1-diyl)}]}bis[1,4,7,10-tetraazacyclododecane-1,4,7-triacetato (4-)]}digadolinium, disodium)

1.01 g (10 mmol) of triethylamine is added to 594.8 mg (1 mmol) of 3,3'-(7,12-diethyl-3,8,13,17-tetramethylporphyrin-2,18-diyl)di(propanohydrazide) and 1806 mg (2.2 mmol) of 10-[7-(4-isothiocyanatophenyl)-2-hydroxy-5-oxo-7-(carboxymethyl)-4-aza-heptyl)-1,4,7-tris(carboxylatomethyl)-1,4,7,10-tetraazacyclododecane, Gd complex, sodium salt, produced according to WO 94/07894, Example 1, in 50 ml of water, and it is stirred for 12 hours at room temperature. It is evaporated to the dry state in a vacuum and chromatographed on silica gel (mobile solvent: methanol/water/glacial acetic acid=10/5/1). The product-containing fractions are evaporated to the dry state, the residue is dissolved in 100 ml of water and set at pH 7.2 with 2N sodium hydroxide solution. Then, it is freeze-dried.

Yield: 2.03 g (89% of theory) of a dark brown amorphous powder

Water content: 7.9%

Elementary analysis (relative to anhydrous substance):

| Cld: | C 48.45 | H 5.22 | N 12.28 | S 2.81 | Gd 13.79 | Na 2.02 |
|---|---|---|---|---|---|---|
| Fnd: | C 48.37 | H 5.37 | N 12.15 | S 2.72 | Gd 13.58 | Na 1.75 |

EXAMPLE 8

Production of a formulation of [mu-16,16'-(7,12-diethyl-3,8,13,17-tetramethylporphyrin-2,18-diyl]bis[3,6,9-tris(carboxymethyl)-11,14-dioxo-3,6,9,12,13-pentaazahexadecanoato]}(8-)]} digadolinato (2-), disodium (title compound of Example 1c, WO 94/07894)

50 mmol of the title compound of Example 1c, WO 94/07894, 10 mmol of TRIS buffer (tris-hydroxymethyl-methylamine-hydrochloric acid, pH 7.4) and 120 mmol of mannitol are dissolved in 500 ml of bidistilled water and made up with water to a volume of 1 l in a measuring flask. The solution that is thus obtained is filtered via a 0.2 μm membrane and decanted into vials. A solution that is thus produced can be used directly for photodynamic therapy.

EXAMPLE 9

Production of a formulation of [mu-[{16,16'-[zinc-(7,12-diethyl-3,8,13,17-tetramethylporphyrin-2,18-diyl]bis[3,6,9-tris(carboxymethyl)-11,14-dioxo-3,6,9,12,13-pentaazahexadecanoato]}(8-)]] digadolinato(2), disodium 50 mmol of the title compound of Example 1c, 10 mmol of TRIS-buffer (tris-hydroxymethyl-methylamine-hydrochloric acid, pH 7.4) and 60 mmol of sodium chloride are dissolved in 500 ml of bidistilled water and made up with water to a volume of 1 l in a measuring flask. The solution that is thus obtained is filtered via a 0.2 μm membrane and decanted into vials. A solution that is thus produced can be used directly for photodynamic therapy.

EXAMPLE 10

Phototoxic effect of the compound [mu-16,16'-(7,12-diethyl-3,8,13,17-tetramethylporphyrin-2,18-diyl]bis[3,6,9-tris(carboxymethyl)-11,14-dioxo-3,6,9,12,13-pentaazahexadecanoato]}(8-)]}digadolinato(2-), disodium (Example 1c of WO 94/07894) on a tumor of a hairless mouse Intracutaneous human colon carcinomas (HT-29 P9) are implanted in the sides of 15 hairless mice that weigh 24–30 g. The tumors are allowed to grow to a size of 5–10 mm. The mice are divided into 3 groups of 5 animals each, within whom the tumor size shows a comparable distribution—4.6×5.2 mm² to 7.1×10.8 mm². On days 1 and 3, i.v. substance is administered to the anesthetized animals. In this case, the animals of group 1 receive 2×130 μl of 0.9% NaCl solution, and they remain in the dark for the entire time. The animals of the second group receive 2×130 μl of a 100 mmol solution of the title compound, which corresponds to a dose of 2×0.5 mmol/kg of body weight. In each case, 30 minutes after administration, the animals are exposed to the light of a xenon lamp (8.5 k Lux, 1 cm glass as a UV filter) for 45 minutes. They spend the rest of the test time in the dark. 2×130 μl of a 100 mmol solution of test substance is also injected into the animals of the third group. The animals remain in the dark, however, for the duration of the test. On the 6th day after the substance is administered, the animals are sacrificed in ether. The tumor is measured, examined macroscopically, removed and tested histologically. The findings for groups 1 and 3 are comparable. The tumors continue to flourish. In group 1, the range is 6.5×7.7 mm² up to 8.6×12.0 mm². In the very large tumors, which are fed by numerous blood vessels, small lesions of the skin (possibly bite marks) and in some cases deeper bleeding are evident in the center. The animals do not seem to be impaired by the tumor or treatment and are in good condition. At the time of the sacrifice, the animals of group 3 do not show any discoloration of the skin. The tumors varied in a range of 5.8×7.0 mm² to 9.4×12.0 mm². Histology showed multifocal central necrosis (diameter: 0.1–0.8 mm). With the animals of group 2, the following observations are made:

| Finding 3 days after first use (0.5 mmol/kg + light) | Finding 3 days after second use (day 6) |
| --- | --- |
| Tumor scabbed over. Tears in the skin. | Tumor heavily eroded, scabbed over. Tears in the skin and additional small solid tumor residues. |
| Tumor colored brown, skin closed, no scab | Tumor heavily eroded, scabbed over. Tears in the skin Additional small solid tumor residues |
| No indication of action | Animal dies immediately after second administration |
| No indication of action | Tumor colored brown. Skin closed, no scab |
| Tumor colored brown, skin closed, no scab | Animal dies immediately before second administration |

Comparative measurement of tumor size was no longer possible in view of the extent of the destruction of the tumors. Tumor growth took place, if at all, only in the periphery and in deep tumor layers. At the end of the test, despite the tumor wounds, the three surviving animals do not seem to be impaired by the tumor or the treatment. The muscle tissue under the tumor seems to be undamaged despite radial irradiation. The tumor did not grow into the muscle layer. Histology of the three non-eroded tumors showed multifocal central necrosis. The diameter with 1.5–2.1 mm is considerably larger than it is in the unirradiated animals. The test substance shows strong phototoxic action.

EXAMPLE 11

Determination of the phototoxicity (ED50) of compound Ic of WO 94/07894 (I) and of the title compound of Example 1d) (II) on a tumor cell culture.

In 25 ml culture flasks, a cell culture of human colon carcinoma (HT-29 P9) is reproduced for 3 days at 37° C. The cultures are divided into two groups and mixed with solutions of test substances (50 mmol of porphyrin unit (PE)/l, diluted with fetal calf serum) in increasing amounts (0; 1.5; 5; 8.5; 12; 15.5; 19 μmol of PE/l). The samples are irradiated for three days with a xenon lamp (8.5 k Lux, UV filter). The first group daily received 2 irradiations of 30 minutes each at an interval of 4 hours. For the rest of the time, it remains in the dark in an incubator. The second group is not exposed to light and remains in the dark in the incubator for the entire time. On the fourth day, the cell growth is determined by live-dead coloration and counting with the counting chamber.

The table indicates the concentration at which about half of the cells are no longer vital. (I: Example 1c of DE 4232925; II: Title compound of Example 1d)

| Compound | ED$_{50}$ [μmol of PE/1] |
|---|---|
| I | 6.4 |
| II | 5.1 |

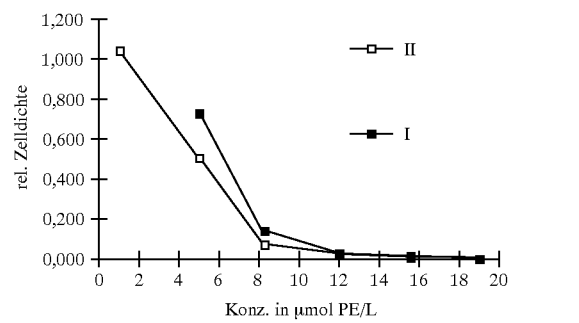

[Key:]
rel. Zelldichte = Relative Cell Density
Konz. in μmol PE/L = Concentration in μmol of PE/1

What is claimed is:

1. In a method of photodynamic therapy comprising administering to a patient a photodynamic agent, the improvement wherein said photodynamic agent is at least one porphyrin complex of formula I:

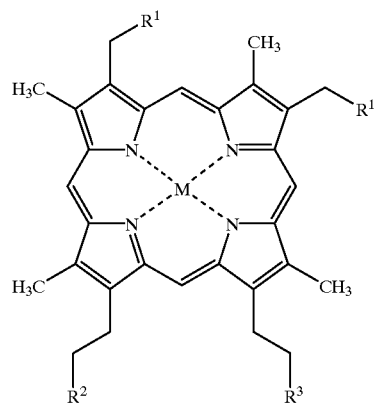

wherein

M stands for two hydrogen atoms or a diamagnetic metal ion, $R^1$ stands for a hydrogen atom, a straight-chain $C_1$–$C_6$ alkyl, a $C_7$–$C_{12}$ aralkyl, or OR', R' is a hydrogen atom or $C_1$–$C_3$ alkyl, $R^2$ stands for —(C=Q)(NR$^4$)$_o$—(A)$_q$—(NR$^5$)—K, —CO—Z or —(NH)$_o$—(A)$_q$—NH—D, Z is —OL, L is an inorganic cation, an organic cation or a $C_1$–$C_4$ alkyl, A means a phenylenoxy group, a $C_1$–$C_{12}$ alkylene which is interrupted by one or more oxygen atoms, or a $C_7$–$C_{12}$ aralkylene that is interrupted by one or more oxygen atoms, o and q, independently of one another, mean numbers 0 or 1, D means a hydrogen atom or —CO—A—(COOL)$_o$—(H)$_m$, with m equal to 0 or 1 and the sum of m and o is equal to 1, $R^3$ stands for —(C=Q) (NR$^4$)$_o$—(A)$_q$—(NR$^5$)—K, Q stands for an oxygen atom or for two hydrogen atoms, $R^4$ means a group —(A)$_q$—H, K means a complexing agent of general formula (IIa), (IIb), (IIc), (IId) or (IIe), whereby if K is a complexing agent of formula (IIa), $R^5$ has the same meaning as $R^4$, and if K is a complexing agent of formula (IIb), (IIc), (IId) or (IIe), $R^5$ has the same meaning as D, provided that a direct oxygen-nitrogen bond is not allowed,

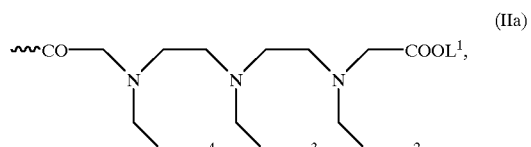

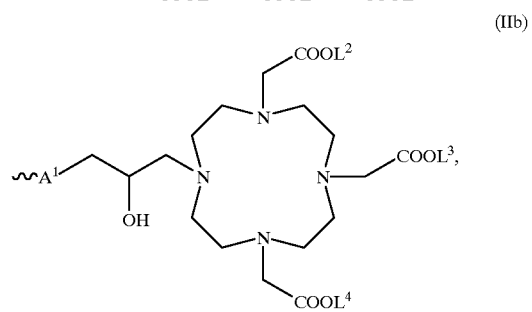

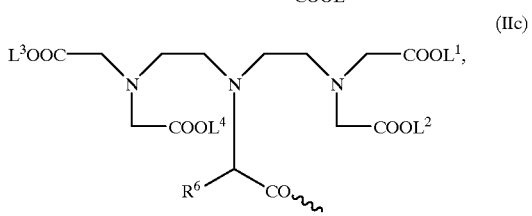

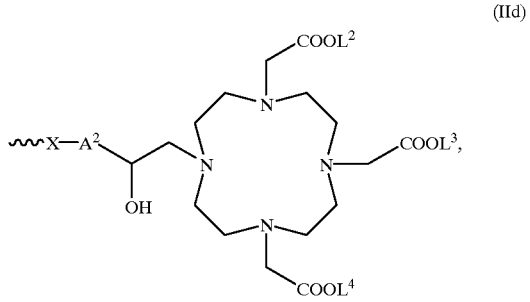

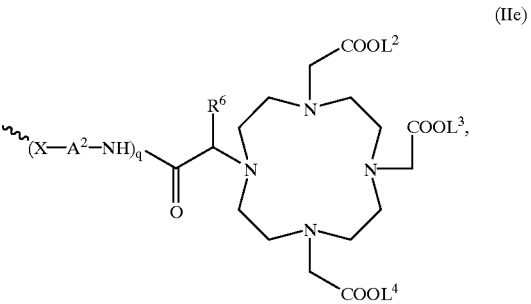

$A^1$ means a phenylenoxy group, a $C_1$–$C_{12}$ alkylene which is interrupted by one or more oxygen atoms, or a $C_7$–$C_{12}$ aralkylene, which is interrupted by one or more oxygen atoms, $R^6$ stands for a hydrogen atom, a straight-chain or branched $C_1$–$C_7$ alkyl, a phenyl or benzyl group, $A^2$ stands for a phenylene, a —$CH_2$—NHCO—$CH_2$—CH($CH_2$COOH)—$C_6H_4$-β-, a phenylenoxy group, or a $C_1$–$C_{12}$ alkylene or $C_7$–$C_{12}$ alkylene that is optionally interrupted by one or more oxygen atoms, 1 to 3 —NHCO, 1 to 3 —CONH and is optionally substituted by 1 to 3 —$(CH_2)_{0-5}$COOH, whereby β stands for the binding site to X, X stands for a —CO— or an NHCS group, and $L^1$, $L^2$, $L^3$ and $L^4$, independently of one another, stand for a hydrogen atom or a metal ion equivalent of an element of atomic numbers 20-32, 37-39, 42-51 or 57-83, provided that at least two of $L^1$, $L^2$, $L^3$ and $^4$ stand for said metal ion equivalents, and that other anions are present to compensate for optionally present charges in the metalloporphyrin, and free carboxylic acid groups that are not required for complexing are optionally present as salts with physiologically compatible inorganic cations, or organic cations, or as esters or amides.

2. A method according to claim 1, wherein M stands for a $Zn^{2+}$, $Sn^{2+}$, $Sn^{4+}$, $Cd^{2+}$, $Mg^{2+}$, $Al^{3+}$, $Lu^{3+}$, $In^{3+}$, $B^{3+}$ or $Ga^{3+}$ ion.

3. A method according to claim 1, wherein $R^2$ and $R^3$ are each —CONHNHK, —CONH$(CH_2)_2$NHK, —CONH$(CH_2)_3$NHK, —CONH$(CH_2)_4$NHK or —CONH$(CH_2)_2$O$(CH_2)_2$NHK.

4. A porphyrin-complex of formula I:

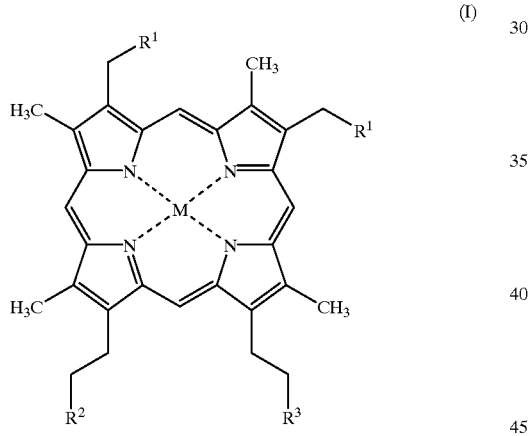

(I)

wherein

M stands for two hydrogen atoms or a diamagnetic metal ion, $R^1$ stands for a hydrogen atom, a straight-chain $C_1$–$C_6$ alkyl, a $C_7$–$C_{12}$ aralkyl, or OR', R' is a hydrogen atom or $C_1$–$C_3$ alkyl, $R^2$ stands for —(C=Q) $(NR^4)_o$—$(A)_q$—$(NR^5)$—K, —CO—Z or —$(NH)_o$—$(A)_q$—NH—D, Z is —OL, L is an inorganic cation, an organic cation or a $C_1$–$C_4$ alkyl, A means a phenylenoxy group, a $C_1$–$C_{12}$ alkylene which is interrupted by one or more oxygen atoms, or a $C_7$–$C_{12}$ aralkylene that is interrupted by one or more oxygen atoms, o and q, independently of one another, mean numbers 0 or 1, D means a hydrogen atom or —CO—A—$(COOL)_o$—$(H)_m$, with m equal to 0 or 1 and the sum of m and o is equal to 1, $R^3$ stands for —(C=Q) $(NR^4)_o$—$(A)_q$—$NR^5$)—K, Q stands for an oxygen atom or for two hydrogen atoms, $R^4$ means a group —$(A)_q$—H, K means a complexing agent of general formula (IIc), (IId), or (IIe), whereby $R^5$ has the same meaning as D, provided that a direct oxygen-nitrogen bond is not allowed,

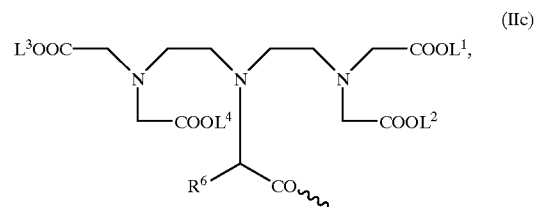

(IIc)

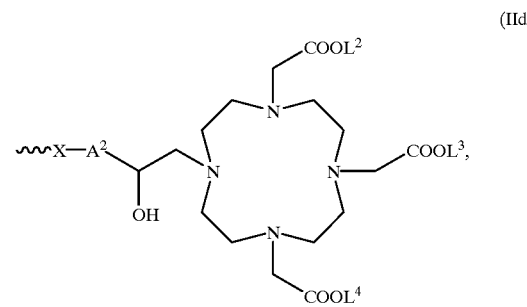

(IId)

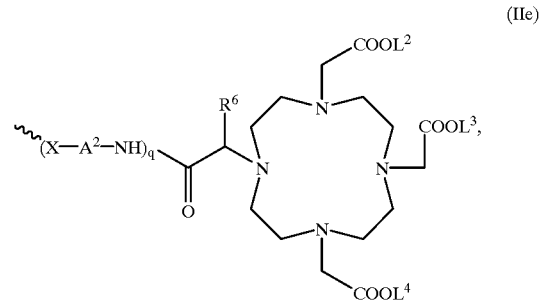

(IIe)

$A^1$ means a phenylenoxy group, a $C_1$–$C_{12}$ alkylene which is interrupted by one or more oxygren atoms, or a $C_7$–$C_{12}$ aralkylene, which is interrupted by one or more oxygen atoms, $R^6$ stands for a hydrogen atom, a straight-chain or branched $C_1$–$C_7$ alkyl, a phenyl or benzyl group, $A^2$ stands for a phenylene, a —$CH_2$—NHCO—$CH_2$—CH($CH_2$COOH)—$C_6H_4$-β-, a phenylenoxy group, or a $C_1$–$C_{12}$ alkylene or $C_7$–$C_{12}$ alkylene that is optionally interrupted by one or more oxygen atoms, 1 to 3 —NHCO, 1 to 3 —CONH and is optionally substituted by 1 to 3 —$(CH_2)_{0-5}$COOH, whereby β stands for the binding site to X, X stands for a —CO— or an NHCS group, and $L^1$, $L^2$, $L^3$ and $L^4$, independently of one another, stand for a hydrogen atom or a metal ion equivalent of an element of atomic numbers 20-32, 37-39, 42-51 or 57-83, provided that at least two of $L^1$, $L^2$, $L^3$ and $L^4$ stand for said metal ion equivalents, and that other anions are present to compensate for optionally present charges in the metalloporphyrin, and free carboxylic acid groups that are not required for complexing are optionally present as salts with physiologically compatible inorganic cations, or organic cations, or as esters or amides.

5. A complex according to claim 4, wherein $A^2$ stands for a —$CH_2$—, —$(CH_2)_2$—, —$CH_2OC_6H_4$-β, —$CH_2OCH_2$—, —$C_6H_4$—, or $CH_2$—NHCO—$CH_2$—CH($CH_2$COOH)—$C_6H_4$-β group, whereby β stands for the binding site to X.

6. A complex according to claim 4, wherein X stands for a CO group.

7. A complex according to claim 4, wherein $R^6$ stands for a hydrogen atom or a methyl group.

8. A method according to claim 1, wherein said complex is {mu-[{16,16'-(7,12-diethyl-3,8,13,17-tetramethylporphyrin-2,18-diyl]bis[3,6,9-tris(carboxymethyl)-11,14,-dioxo-3,6,9,12,13-pentaazahexadecanoato]}(8-)]}digadolinato(2-), disodium.

9. A method according to claim 1, wherein said complex is {mu-[{16,16'-[zinc(II)-7,12-diethyl-3,8,13,17-tetramethylporphyrin-2,18-diyl]bis[3,6,9-tris(carboxymethyl)-11,14-dioxo-3,6,9,12,13-pentaazahexadecanoato]}(8-)]}digadolinato, disodium.

10. A method according to claim 1, wherein said complex is {mu-[{16,16'-(7,12-diethyl-3,8,13,17-tetramethylporphyrin-2,18-diyl]bis[3,6,9-tris(carboxymethyl)-11,14-dioxo-3,6,9,12,13-pentaazahexadecanoato]}(8-)]}digadolinato(2-), disodium.

11. A method according to claim 1, wherein said complex is {mu-[{16,16'-[zinc(II)-7,12-diethyl-3,8,13,17-tetramethylporphyrin-2,18-diyl]bis[3,6,9-tris(carboxymethyl)-11,14,dioxo-3,6,9,12,13-pentaazahexadecanoato]}(8-]}digadolinato, disodium.

12. A method according to claim 1, wherein three of the groups $L^1$, $L^2$, $L^3$ and $L^4$ are metal ion equivalents of chromium (III), manganese (III), iron (III), cobalt (III), neodymium (III), samarium (III), or ytterbium (III).

13. A method according to claim 1, wherein two of the groups $L^1$, $L^2$, $L^3$ and $L^4$ are metal ion equivalents of manganese (II), cobalt (II), nickel (II), copper (II) or praseodymium (II).

14. A method according to claim 3, wherein M stands two hydrogen atoms or $Zn^{2+}$.

15. A method according to claim 4, wherein $R^2$ and $R^3$ are the same.

16. A method according to claim 1, wherein $A^2$ is —$CH_2$—, —$(CH_2)_2$—, —$CH_2OC_6H_4$-β, —$CH_2OCH_2$—$C_6H_4$—, —$CH_2$—NHCO—$CH_2$—CH($CH_2$COOH)—$C_6H_4$-β, whereby β stands for the binding site to X.

17. A method according to claim 1, wherein X is CO.

18. A method according to claim 1, wherein $R^6$ is H or methyl.

19. A method according to claim 1, wherein said complex is administered in an amount of 0.01 μmol–2.0 mmol/kg of body weight.

20. A method of MRI diagnostic monitoring of photodynamic therapy comprising administering to a patient a photodynamic agent, irradiating said agent, and monitoring the photodynamic therapy induced thereby using magnetic resonance imaging, wherein said agent is a complex according to claim 4.

* * * * *